(12) United States Patent
Grafenberg et al.

(10) Patent No.: US 10,682,767 B2
(45) Date of Patent: Jun. 16, 2020

(54) METHODS FOR OPERATING MEDICAL IMAGING DEVICES AND MEDICAL IMAGING DEVICES

(71) Applicant: Siemens Healthcare GmbH, Erlangen (DE)

(72) Inventors: Alexander Grafenberg, Effeltrich (DE); Hans Schweizer, Plattling (DE)

(73) Assignee: Siemens Healthcare GmbH, Erlangen (DE)

( * ) Notice: Subject to any disclaimer, the term of this patent is extended or adjusted under 35 U.S.C. 154(b) by 0 days.

(21) Appl. No.: 16/101,673

(22) Filed: Aug. 13, 2018

(65) Prior Publication Data

US 2019/0054632 A1    Feb. 21, 2019

(30) Foreign Application Priority Data

Aug. 15, 2017   (EP) .................................... 17186303

(51) Int. Cl.
*B25J 13/08*   (2006.01)
*G16H 20/17*   (2018.01)
(Continued)

(52) U.S. Cl.
CPC .......... *B25J 13/08* (2013.01); *G02B 27/0172* (2013.01); *G02B 27/0179* (2013.01);
(Continued)

(58) Field of Classification Search
CPC ..... B25J 13/08; G16H 20/17; G02B 27/0172; G06F 3/017; G06T 19/006
(Continued)

(56) References Cited

U.S. PATENT DOCUMENTS

2013/0050258 A1*   2/2013   Liu .................... G02B 27/017
                                                          345/633
2013/0241805 A1*   9/2013   Gomez ................ G09G 3/003
                                                          345/8
(Continued)

FOREIGN PATENT DOCUMENTS

EP    2978218 A1    1/2016
EP    3305232 A1    4/2018
(Continued)

OTHER PUBLICATIONS

Su L-M, Vagvolgyi BP, Agarwal R, Reiley CE, Taylor RH, Hager GD. Augmented reality during robot-assisted laparoscopic partial nephrectomy: toward real-time 3D-CT to stereoscopic video registration. Urology 2009; 73(4):896e900.*
(Continued)

*Primary Examiner* — Jin Ge
(74) *Attorney, Agent, or Firm* — Lempia Summerfield Katz LLC

(57) ABSTRACT

Methods for operating medical imaging devices and medical imaging devices are disclosed herein. In one example, the medical imaging device includes a user interface device for displaying information relevant to an imaging process to a user and/or receiving user input relevant to an imaging process and at least one component controllable according to a user command entered using the user interface device, wherein the user interface device includes at least one pair of mixed reality smart glasses, whereby a virtual assistance line indicating the direction of view of a wearer of the smart glasses is projected into the field of view of the smart glasses, wherein upon reception of at least one user command at least one component is controlled based on the user command and the direction defined by the assistance line.

18 Claims, 2 Drawing Sheets

(51) Int. Cl.
*G16H 30/20* (2018.01)
*G02B 27/01* (2006.01)
*G06F 3/01* (2006.01)
*G06T 19/00* (2011.01)
*G06F 3/0484* (2013.01)
*G06F 3/0485* (2013.01)

(52) U.S. Cl.
CPC ............ *G06F 3/017* (2013.01); *G06T 19/006* (2013.01); *G16H 20/17* (2018.01); *G16H 30/20* (2018.01); *G02B 2027/014* (2013.01); *G02B 2027/0141* (2013.01); *G02B 2027/0178* (2013.01); *G02B 2027/0187* (2013.01); *G06F 3/0485* (2013.01); *G06F 3/04842* (2013.01); *G06T 2200/24* (2013.01)

(58) Field of Classification Search
USPC ........................................................ 345/633
See application file for complete search history.

(56) References Cited

U.S. PATENT DOCUMENTS

| 2014/0022283 | A1 | 1/2014 | Chan et al. | |
|---|---|---|---|---|
| 2014/0168056 | A1 | 6/2014 | Swaminathan | |
| 2015/0350413 | A1 | 12/2015 | Ma | |
| 2016/0246055 | A1* | 8/2016 | Border | G02B 27/017 |
| 2016/0257000 | A1 | 9/2016 | Guerin | |
| 2016/0321841 | A1* | 11/2016 | Christen | G06T 19/006 |
| 2017/0039321 | A1* | 2/2017 | Reicher | G06F 16/245 |
| 2017/0206691 | A1* | 7/2017 | Harrises | G06T 11/60 |
| 2017/0367771 | A1* | 12/2017 | Tako | A61B 34/20 |
| 2019/0025588 | A1* | 1/2019 | Osterhout | H04N 13/383 |

FOREIGN PATENT DOCUMENTS

| WO | WO2011125007 A1 | 10/2011 |
|---|---|---|
| WO | WO2015008164 A2 | 1/2015 |

OTHER PUBLICATIONS

Nicolau, S., Soler, L., Mutter, D., Marescaux, J., 2011. Augmented reality in laparoscopic surgical oncology. Surg. Oncol. 20, 189-201.*

Rosenthal, Michael et al., "Augmented Reality Guidance for Needle Biopsies: A Randomized, Controlled Trial in Phantoms." Proceedings of MICCAI 2001, eds. W. Niessen and M. Viergever, Lecture Notes in Computer Science, 2001, vol. 2208, pp. 240-248.*

European Search Report for corresponding Application No. 17186303.8-1126, dated Feb. 22, 2018.

Y, Ro et al. "Augmented Reality Smart Glasses Definition Conceptual Insights and Managerial Importance." ResearchGate, available at: https://www.researchgate.net/publication/279942768, pp. 1-21 (Jul. 2015).

European Office Action for European Application No. 17 186 303.8—1126 dated Jan. 20, 2020.

* cited by examiner

METHODS FOR OPERATING MEDICAL IMAGING DEVICES AND MEDICAL IMAGING DEVICES

The application claims the benefit of European Patent Application No. EP 17186303.8, filed Aug. 15, 2017, which is hereby incorporated by reference in its entirety.

TECHNICAL FIELD

The disclosure relates to methods for operating a medical imaging device, wherein the medical imaging device includes a user interface device for displaying information relevant to an imaging process to a user and/or receiving user input relevant to an imaging process and at least one component controllable according to a user command entered using the user interface device, and wherein the user interface device includes at least one pair of mixed reality smart glasses. The disclosure also relates to medical imaging devices.

BACKGROUND

Current medical imaging devices offer a considerable number of functions and accordingly a considerable number of complex operating elements, which a user may use to configure and realize these functions. For example, embodiments of imaging processes and thus the imaging parameters vary greatly depending on the area imaged and the diagnostic goal. While common imaging processes are already hard to operate, this problem grows more severe if the medical imaging device is used in sterile environments, (e.g., during a surgical intervention). For example, medical imaging devices having a c-arm and a mobile carrier for the c-arm may be used as interventional modalities. In such an environment, an operating device or system has to be provided which on the one hand allows ergonomic use of the complex functions, on the other hand fulfils the requirements for a sterile operation.

In this context, it has been proposed to use mixed reality smart glasses as an operating element of the user interface device. For example, German Patent Application DE 10 2017 202 517.4 (published as EP 3305232) proposes to have at least one pair of mixed reality smart glasses as part of the user interface device.

The mixed reality smart glasses are configured to display at least part of the imaging process relevant information and/or to receive at least part of the imaging process relevant user input. Such mixed reality smart glasses have already been proposed in the state of the art, are a type of head mounted display, and may also be termed augmented reality smart glasses. Such smart glasses are, for example, available as "HoloLens" (Microsoft) or "MetaVision". These devices may be worn covering the eyes of the user. An augmented reality is provided by projecting additional computer-generated information into the field of view of the user. Such a pair of smart glasses may include a plurality of sensors, in particular 3D and/or RGB cameras and/or at least one movement sensor for tracking the head wearing the smart glasses. The pair of smart glasses additionally includes projection units for each eye providing stereoscopic view, a control device, and/or a speaker/microphone. The control unit of the smart glasses may be configured to map augmented reality objects to the, in particular, sensed environment geometry and to display perspectively correct and stereoscopic graphical elements (e.g., augmented reality objects) using the projection units. The control unit may further be configured to detect and identify operating gestures performed by the user. It is noted that the control unit or at least parts of the control unit may also be located externally to the smart glasses, (e.g., inside a computing device). This is also possible for sensors. For example, an "inside-out" tracking of the smart glasses may be supported or replaced by external tracking devices ("outside-in" tracking), for example, by using externally trackable markers on the smart glasses. This may improve accuracy of tracking.

It has also been proposed to have more than one user wearing such smart glasses. These pairs of smart glasses may communicate directly or indirectly, allowing to match the augmented realities created for each user. Thus, all users see the same objects/graphical elements, configured to their respective point of view.

German Patent Application DE 10 2017 202 517.4 (published as EP 3305232) proposes to use such a pair of smart glasses to improve imaging processes in view of operation of the medical imaging device as well as informing the user.

A general problem in imaging systems is the presence of multiple moving components to establish different imaging geometries. An example is, again, a c-arm device. To provide the optimal medical information, imaging directions have to be chosen carefully. A further problem, in particular in 3D imaging, is the orientation of views of three-dimensional image data sets on corresponding display devices, (e.g., monitors). In certain systems, the view may be rotated by using a mouse or touchscreen, but this takes a long time to find the optimal direction. It has been proposed to use algorithms in medical imaging devices, which may automatically detect instruments or implants used in minimally invasive interventions and choose display orientations of three-dimensional image data sets accordingly. However, these methods may fail when used in workflows for which they have not been optimized or designed, for example, choosing a viewing direction when instruments or implants are not yet visible in image data.

SUMMARY AND DESCRIPTION

It is an object of the disclosure to provide an improved tool for users to define directions when operating a medical imaging device.

The scope of the present disclosure is defined solely by the appended claims and is not affected to any degree by the statements within this description. The present embodiments may obviate one or more of the drawbacks or limitations in the related art.

In a method for operating a medical imaging device, the medical imaging device includes a user interface device for displaying information relevant to an imaging process to a user and/or receiving user input relevant to an imaging process and at least one component controllable according to a user command entered using the user interface device. The user interface device includes at least one pair of mixed reality smart glasses. In the method, it is provided to project a virtual assistance line indicating the direction of view of a wearer of the smart glasses into the field of view of the smart glasses, wherein, upon reception of at least one user command, at least one component is controlled based on the user command and the direction defined by the assistance line.

It is proposed to add an assistance line as an additional tool in the augmented environment created by the mixed reality smart glasses, which is perfectly suited for defining directions while operating the imaging device. The assistance line corresponds to the current viewing direction of the user wearing the smart glasses, providing the illusion of a virtual vector or laser ray emanating between the eyes of the user, providing a clear indication of a direction. The virtual assistance line moves corresponding to the movement of the user (and thus the smart glasses), such that it may be adjusted by adjusting the own position and view of the user. It is thus possible to, for example, align the assistance line with anatomy of the patient and/or a medical instrument used in a minimally invasive intervention.

The assistance line, as a graphical element/augmented reality object, is projected into the field of view using the corresponding projection units of the smart glasses, controlled by a control unit of the smart glasses. The correct projection position/orientation of the assistance line may be updated, (e.g., cyclically), based on the current position and orientation of the smart glasses. It is also possible to use further information to refine the positioning of the assistance line as a graphical element, for example, by taking into account data of an eye sensor, further indicating the direction of view of the user. In summary, an intuitive way of defining a direction by a user is provided.

A field of application may be x-ray imaging devices, such that in one embodiment, the medical imaging device is an x-ray device (e.g., mobile x-ray device), in particular, configured for intraprocedural imaging, wherein at least one of the components is or constitutes an imaging assembly including at least an x-ray source and an x-ray detector and, in particular, also a c-arm. Such mobile c-arm x-ray devices are complex to operate because many degrees of freedom exist, in particular, regarding the imaging geometry. Certain components, (e.g., at least the x-ray source and detector or the c-arm), are moveable to define imaging geometries for the imaging process. In this context, user commands may define movement of such components. The disclosure may also be applied to stationary c-arms. Although most of the embodiments mentioned in this description may relate to x-ray medical imaging devices, the disclosure is also applicable to other medical imaging modalities such as ultrasound or magnetic resonance imaging.

In one embodiment, the direction of view of the wearer is defined as being perpendicular to a connecting axis of the eyes at a center point between the eyes. In this manner, the virtual assistance line has a predetermined relationship to the smart glasses and may be calculated when the position and orientation of the smart glasses are known. This position and orientation may be determined by "inside out" tracking, "outside in" tracking, or a combination thereof.

The assistance line may only be shown when a corresponding operating mode has been activated by the user wearing the smart glasses. For example, this operating mode may be a direction defining operation mode. Every time the user wants to define a certain direction, such as for defining acquisition parameters or display parameters, the user may activate the corresponding operating mode. Upon activation, the virtual assistance line is added as a graphical element to the augmented reality environment. While the definition of a direction using the assistance line is not needed, the corresponding operating mode is deactivated and the virtual assistance line does not disturb the user when operating other functions of the augmented reality created by the smart glasses or reading information provided by it.

In an embodiment, a fixing user command is provided, upon reception of which the current position of the projected assistance line is held in place independently of any movement of the smart glasses. In this manner, the user may interact with the user interface device, (e.g., using a spoken user command or a gesture), to fix the virtual assistance line in its current position and direction. If the user moves their head now, the smart glasses use their stereoscopic projection units to create the illusion of the virtual assistance line being stationary where it was fixed by using the fixing user command. The user may now more easily and intuitively examine the fixed direction from multiple viewing angles, judging its suitability for the function aimed at. If the user is content with the chosen direction, the user may use the user command finally selecting the current direction defined by the virtual assistance line to perform this function. Of course, it is also possible to provide an unfix user command such that a fixed virtual assistance line may be released from its fixed position and once again be projected as the current direction of view of the user.

Solid real and/or virtual objects in this field of view may be detected and the projection of the assistance line may be cut off where it interacts with at least part of these objects. Modern smart glasses may have a high quality 3D detection capability, (e.g., using 3D cameras), so that the position of solid objects in the field of view of the user may be derived. It is possible to project the virtual assistance line in a manner such that solid objects, (e.g., the patient), are excluded from the projection of the line. In other words, the virtual assistance line is invisible where the solid object, (e.g., the patient), is and virtually emerges from the patient again at the other end. The augmented reality is thus created more realistically, in particular, in the case of a fixed virtual assistance line.

To use the direction currently defined by the virtual assistance line, at least one selection user command may be provided, upon detection of which the current direction of the line is used for performing a function associated which the selection user command detected. In particular, multiple selection user commands may be defined such that directions may be defined for different applications. While the selection user command (and the fixing and/or unfixing user command, if provided) may be spoken user commands and/or gestures, it is also possible to provide other operating elements for performing these user commands, (e.g., hardware input devices like hand- or foot-operated switches and the like). By providing selection user commands, the direction defined by the current virtual assistance line may be used for several functions/tasks of the medical imaging device.

In an embodiment, upon detection of a corresponding selection user command, at least one geometric acquisition parameter of the medical imaging device is selected dependent on the direction of the assistance line and/or at least one interventional component of the medical imaging device, (e.g., a robot), is adjusted dependent on the direction of the assistance line. The alignment of the medical imaging device, (e.g., the imaging system, and/or a medical instrument, such as a robot), may thus be defined along the virtual assistance line. For example, after using a secure further input or user command, a c-arm of the medical imaging device and/or an automated patient table may be controlled as components of the medical imaging device to align the central beam of the medical imaging device with the direction defined by the virtual assistance line. It may be provided to calculate required motion of the components of the medical imaging device by sensing current positions of these components by sensors of the smart glasses and taking into account the known position of the virtual assistance line. This embodiment is not restricted to defining x-ray projection directions in the medical imaging device but may also advantageously be applied to medical instruments used in minimally invasive interventions surveyed by the medical imaging device. In an embodiment, the medical imaging device is a c-arm device, wherein the geometric acquisition parameters are chosen and the c-arm is adjusted such that the acquisition direction corresponds to the direction of the assistance line. It is, again, noted that the control of the c-arm or other components to realize the acquisition direction may be performed later at a stage when no persons are subject to possible collisions, in particular, when a further user command is received.

If the assistance line is used, for example, as a virtual central beam defining a projection direction, an additional graphical element representing an isocenter as virtual object may be provided on the assistance line, the position of which may be adjusted using (e.g., hand) gestures and/or other adjustment commands. For example, the assistance line may be fixed using a fixing command, wherein the additional graphical element may be provided and manipulated.

As already indicated, the direction defined by the virtual assistance line may also be used for displaying functions. In an embodiment, upon detection of a corresponding selection user command, at least one geometrical display parameter for displaying an image data set on a display device of the user interface device is chosen dependent on the direction of the virtual assistance line. This advantageously allows to correlate viewing directions of the user onto the patient still present in the medical imaging device, (e.g., during an intervention), and in particular three-dimensional data sets of the patient. Thus, in an embodiment, the image data set is a three-dimensional image data set of a patient currently imaged with the medical imaging device and registered to a current position of the patient, wherein the direction of the assistance line defines a viewing direction of the presentation of the three-dimensional data set or a slice stacking direction, in particular for a multi planar reformation (MPR), as the geometric display parameter. Alternatively, concerning MPR, slice stacking directions may also be defined, for example, as being perpendicular to the current direction of the virtual assistance line. This embodiment may allow the user to scroll through MPR slices along the direction defined by the virtual assistance line. It is also possible to align the three-dimensional image data set of the patient such that the user may view the image data set exactly in the relevant viewing direction on the display device, or that the user may scroll through slice images in planes perpendicular to this relevant viewing direction.

In the case of the assistance line direction defining a slice stacking direction, additional scrolling user commands, (e.g., gestures), may be provided, wherein upon detection of a scrolling user command, an adjacent slice in a scrolling direction associated with or derivable from the scrolling user command is displayed. Thus, scrolling through slice images (or sectional images), in particular using MPR, may also be integrated into the herein described user interface concept.

Also, the smart glasses may be used as the or part of the display device, wherein the image data is a three-dimensional image data set of a patient currently imaged with the medical imaging device and registered to a current position of the patient and the image data set is projected into the field of view to appear at a position of the patient corresponding to the region of the patient shown in the image data set. In particular, this presentation of the three-dimensional image data set may be realized contact analogue. In this embodiment, the interaction and display of a particular slice image is realized by the smart glasses, overlaid onto the actual acquisition region of the patient, so that the user is provided with the illusion of viewing the three-dimensional image data set where it was acquired.

It is noted that, in a case wherein the user wishes to edit or readjust the direction defined by the virtual assistance line, an editing operating mode of the user interface device may be provided, wherein, for example, by using gestures and/or spoken commands, the user may adjust the position and orientation of a direction defined by the virtual assistance line.

In a further embodiment, as a special case of an editing operating mode, a remote control mode of the user interface device is available which may be activated by the user, upon activation of which changes in the direction of view of the user are detected and an, in particular previously fixed by using a fixing command, assistance line, which does not indicate the direction of view of the user, but is otherwise positioned in the field of view of the user, is moved according to the detected changes. In this case, an assistance line that does not correspond to the direction of view of the user may be manipulated by changing the direction of view of the user, in particular, by movement of the head of the user wearing the smart glasses. In particular, the remotely controllable assistance line may have another origin or viewpoint from which it originates. The direction of this remotely controllable assistance line as well as its viewpoint may be manipulated by the user, moving his head and/or otherwise detectably changing his own viewpoint/direction of view.

This advantageously allows to also define directions which would otherwise not or only uncomfortably be definable. For example, if a user wants to define a vertical direction through the patient, he would have to move his head above (or below) the patient, which is not desirable. By providing the remote control mode, the user may position an assistance line as his direction of view in a comfortable way, fix the assistance line by using a fixing command, and activate the remote control mode to control the now remotely controllable assistance line's geometry by moving his head accordingly. In the example mentioned above, the assistance line may be locked in a 45° position to the patient, the remote control mode may be activated with respect to the fixed assistance line, and head movement/rolling is detected to adjust its position. In other words, the relative movement of the head of the user is measured by the smart glasses and used for alignment of the assistance line as desired by the user. This makes the head an operating element, like a joystick, for the assistance line.

It is noted that this remote control feature may also be used for other virtual objects/graphical elements, (e.g., isocenter positions), as discussed above, which may also be manipulated remotely using the head as operating element.

In an embodiment, multiple assistance lines are projected at the same time, corresponding to different users wearing smart glasses and/or including assistance lines held in position due to a corresponding fixing user command. It is possible to define multiple virtual assistance lines, for example, by fixing previous virtual assistance lines in place using a fixing user command and adding additional virtual assistance lines based on the current viewing direction of the user. In this manner, for example, multiple acquisition geometries to be used in succession may be defined by a user as acquisition parameters of the medical imaging device, wherein these acquisition geometries may later be automatically realized by corresponding control of components of the medical imaging device. The method may also be used to view these directions using a three-dimensional image data set of the patient already available before a minimally-invasive intervention, which is registered to the actual patient position in the medical imaging device, so that finding anatomical structures during the intervention may be facilitated. Additionally, or in an alternative embodiment, multiple users wearing smart glasses may view virtual assistance lines of other users, such that the herein described system may also be used to mark relevant points and/or orientations and communicate their position to other users.

In a further embodiment, at least one geometry information regarding at least one assistance line is calculated and projected into the field of view of the smart glasses. Such geometry information may describe relationships between at least two lines, (e.g., parallelism, distance, relative angles, symmetry, and the like). Thus, further geometric aids may be provided to the user. These tools may be used to measure length and/or geometric relationships of multiple virtual assistance lines, respectively, or from assistance lines to other geometry structures present in the field of view, in particular, real objects and/or other graphical elements/augmented reality objects.

Such additional augmented reality objects may include alignment aiding lines, such that a virtual assistance line may be aligned with an alignment aiding line, which may be an optimal viewing direction onto the patient during an intervention.

The disclosure also includes a medical imaging device having a user interface device for displaying information relevant to an imaging process to a user and/or receiving user input relevant to an imaging process, at least one component controllable according to a user command entered using the user interface device, and a control device, wherein the user interface device includes at least one pair of mixed reality smart glasses and the control device is configured to perform a method. In particular, the control device configured to perform a method may include the control unit of the smart glasses. All remarks and embodiments concerning the method may also be applied to the medical imaging device such that the same advantages may be achieved.

BRIEF DESCRIPTION OF THE DRAWINGS

Further details and advantages of the disclosure be taken from the following description of embodiments in conjunction with the drawings, in which.

DETAILED DESCRIPTION

Figure 1:
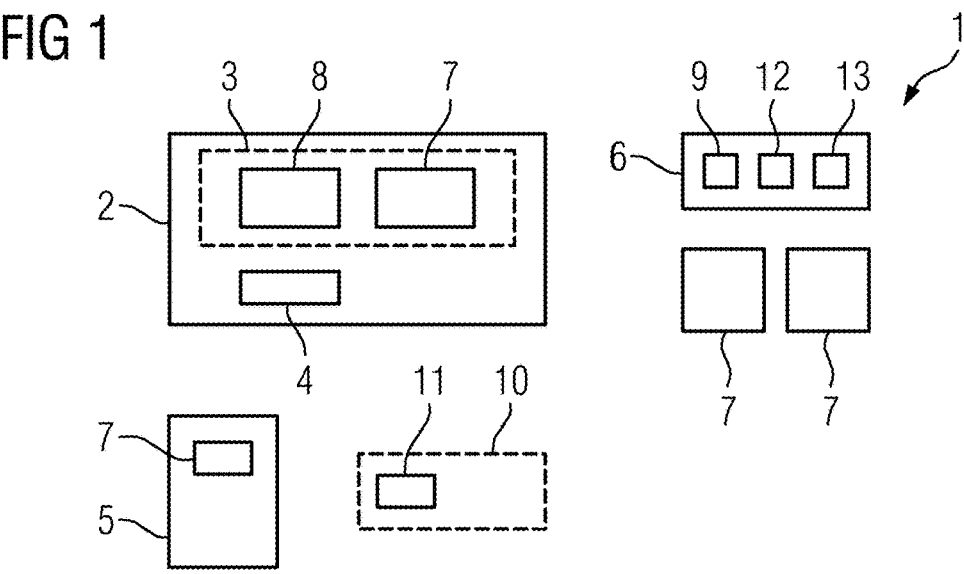
FIG. 1 depicts an example of components of a medical imaging device.

FIG. 1 is a drawing depicting components of a medical imaging device 1. The imaging device 1 includes an imaging apparatus 2. The imaging apparatus 2 includes an image acquisition unit 3 (e.g., as imaging assembly) and a patient table 4. Further principal components of the medical imaging device 1 include a display trolley 5 (also called monitor trolley), which is mobile and on which multiple displays are mounted. The display trolley 5 is part of a user interface device for displaying information and receiving user input relating to imaging processes. The user interface device further includes at least one pair of mixed reality smart glasses 6 and multiple optional operating elements 7, for example, hand- and/or foot-operated switches, microphones, and/or cameras for receiving gestures and/or spoken commands and the like.

In this embodiment, the medical imaging device 1 is an x-ray device having a c-arm 8 mounted to a mobile carrier. An x-ray detector and an x-ray receiver are mounted to opposing ends of the c-arm 8. The medical imaging device 1 is suited and configured for imaging survey during a minimally invasive intervention on a patient positioned on the patient table 4.

The medical imaging device 1 is controlled by a distributed control device 10, which also includes a control unit 11 for the smart glasses 6, which may at least in part be integrated into the smart glasses 6.

The mixed reality smart glasses 6 may be of any type already known, for example "HoloLens" by "Microsoft". The smart glasses 6 in this case include projection units 9 for both eyes, sensors 12 for acquiring sensor data regarding the environment, the user of the smart glasses 6, movement of the smart glasses 6 for tracking purposes and/or further information, and optionally acoustic equipment 13 including a speaker and a microphone. The sensors 12 may include at least one 3D camera.

The control unit 11 is configured to map augmented reality objects, in this case graphical elements including information elements and interactive virtual operating elements, to the environment geometry measured using sensors 12, so that the augmented reality objects may be projected accurately and using the correct perspective by the projection units 9. The control unit 11 further evaluates sensor data of the sensors 12 to detect interaction of the user with virtual operating elements and/or other gestures which may be interpreted as user commands. As such, smart glasses 6 are in principle already known in the state of the art, they shall not be discussed further.

Figure 2:
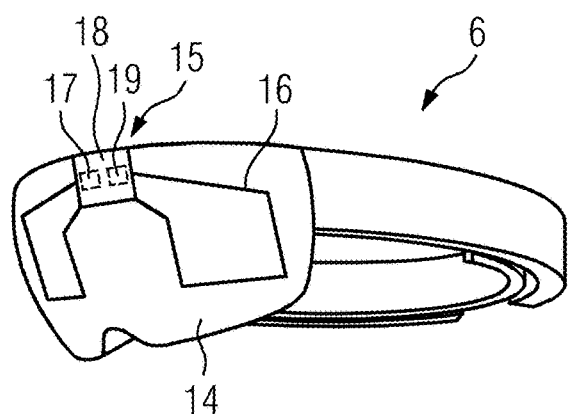
FIG. 2 depicts a first view of an exemplary pair of smart glasses.
Figure 3:
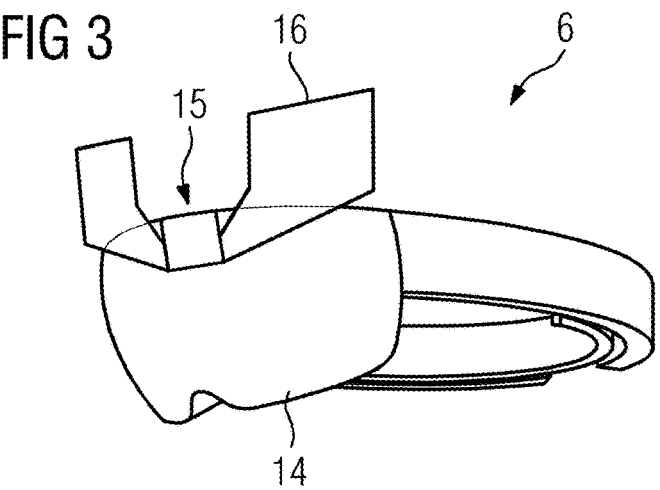
FIG. 3 depicts a second view of the exemplary smart glasses.

FIG. 2 depicts a perspective view of the smart glasses 6. The smart glasses 6 include a visor 14 through which the user may see the environment in his field of view and which is also used as projection surface for the projection units 9. The smart glasses 6 further include a holding device or mechanism 15 in the form of a mounting bracket, which holds an accessory 16. The accessory 16, (which may be a magnifying accessory, a filter accessory, and/or a protection accessory), is mounted removably to the holding device 15 using a magnetic quick fastener 18. A positioning device 17 facilitates pivoting the holding device 15, allowing the accessory 16 to be swung out of the field of view of the user as shown in FIG. 3.

The positioning device 17 may include a motor 19 allowing automatic pivoting of the accessory 16 out of the field of view of the user and into the field of view of the user. This automatic movement may be effected after detecting a user command, (e.g., a gesture and/or voice command), by evaluating sensor data of the sensors 12.

It is noted that the smart glasses 6 may additionally or alternatively include further holding device or mechanism, (e.g., a holding device for a head lamp as accessory).

A graphical element (e.g., augmented reality object) is used to aid a user, in particular a person performing a minimally invasive intervention, in intuitively defining directions for use with functions of the medical imaging device 1. This graphical element is a virtual assistance line corresponding to the direction of view of the user, as shown schematically in FIG. 4. In this figure, a user 20 is shown wearing the smart glasses 6 and standing close to the patient table 4, where a minimally-invasive intervention on a patient 21 positioned on the patient table 4 is to be performed. The user 20 uses a medical instrument 22, (e.g., a needle).

Upon activating a direction defining operation mode of the user interface device by performing a corresponding user command, a virtual assistance line 23 is projected into his field of view using the projection units 9. The virtual assistance line 23 is defined as being perpendicular to a connection axis of the eyes at a center point between the eyes. In other embodiments, if the smart glasses 6 also have an eye sensor, it is conceivable to use the actual direction of view of the user 20.

The virtual assistance line 23 moves with the head of the user, such that an intuitive way of defining a direction in three-dimensional space is provided. If the user wants to more closely examine a current direction of the virtual assistance line 23, the user may use a fixing user command, which may be a spoken command and/or a gesture, to "freeze" the current position and orientation of virtual assistance line 23 in space and assess the defined direction from multiple different viewpoints. Additional virtual line 24 shown in FIG. 4 may be such a line held fast in augmented reality space, where a new current virtual assistance line 23 has been added by a corresponding user command. Virtual line 24 may also be an alignment aiding line or may be defined by another user wearing additional smart glasses, thus also able to define a virtual assistance line which may be shown in the augmented realities of other users 20.

Line 23 may also be another reference line, for example, providing geometry information as a horizontal line or the like. Additional geometry information describing the relationship between any virtual lines 23, 24 shown may also be derived and added as corresponding graphical elements/augmented reality objects, such as the angle 25 between lines 23, 24 indicated in FIG. 4.

Figure 4:
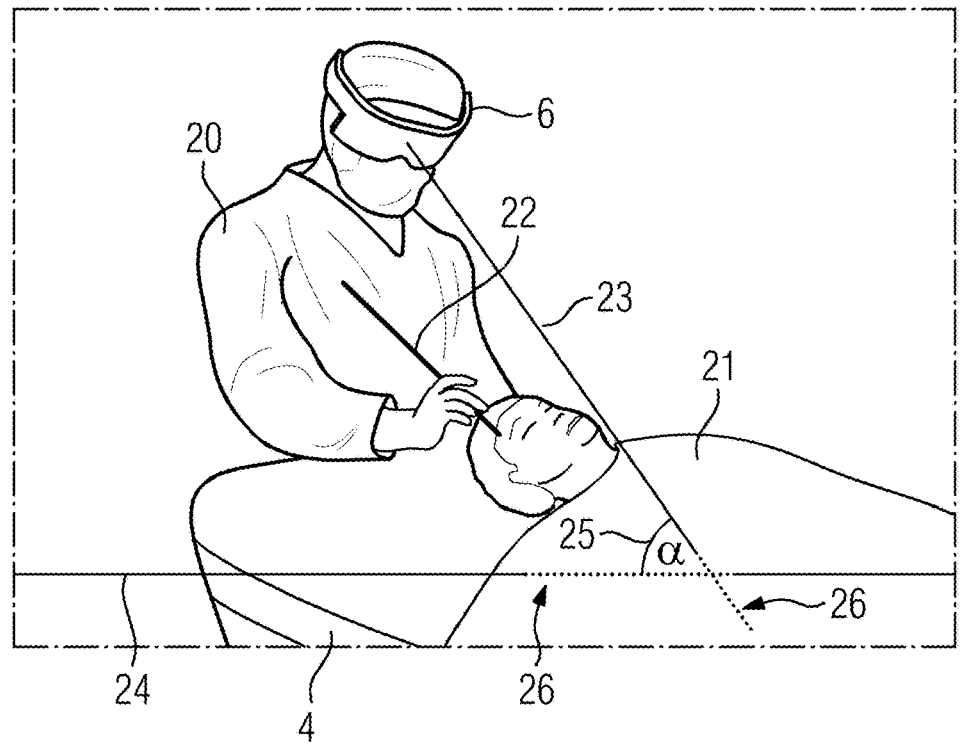
FIG. 4 depicts an example of a person wearing the smart glasses and possible augmented reality objects.

It is also indicated in FIG. 4 by dotted sections 26 of lines 23, 24 that lines 23, 24 are hidden, (not shown), when it is determined that they intersect a solid body, (e.g., the patient 21). The line 23, 24 may be shown again once their course leaves a corresponding solid object.

If one of multiple selection user commands is given by the user 20 and thus detected by the user interface device, the current direction of the virtual assistance line 23, be it fixed in space or not, is used for performing a function associated with the detected selection user command.

The direction of the virtual assistance line 23 may, in a first example, be used to define geometric acquisition parameters of the medical imaging device 1, in this case for example, an acquisition direction (projection direction) to be realized by corresponding movement of the c-arm 8 and/or the patient table 4. Additionally, selection user commands may be provided to align, for example, medical instrument 22 by using a robot (not shown). It is, however, provided, that the geometric acquisition parameters are only chosen when the selection user command is given, wherein the adjustment of the corresponding components is only affected when another user command is performed, in particular, using one of the operating element 7 indicating that the user 20 has moved to a secure position and is not subject to possible collisions with components.

Another area of application for the direction defined by the virtual assistance line 23 is the display of image data sets, which may or may not be acquired using medical imaging device 1 but are registered with the patient 21 positioned on the patient table 4, whereto the smart glasses 6 and thus the virtual assistance line 23 is also registered.

Figure 5:
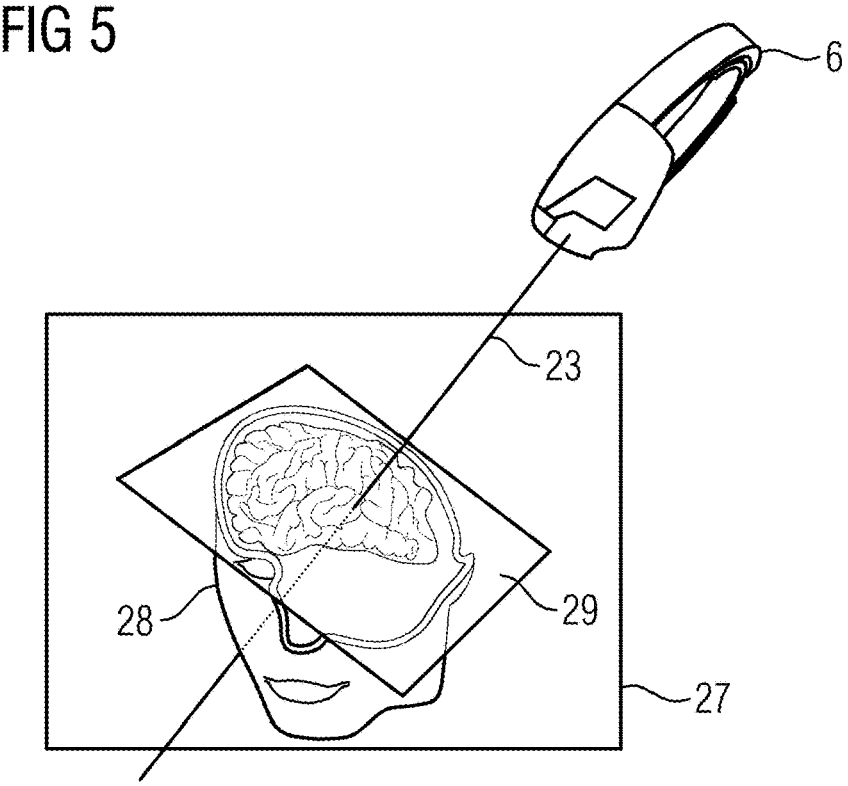
FIG. 5 depicts a possible use of a direction defined by a virtual assistance line.

In FIG. 5, a three-dimensional image data set 27 of the head 28 of the patient 21 is indicated. To display this three-dimensional image data set 27, a multi-planar reformation (MPR) is performed, resulting in a series of slices 29/sectional images extending in planes perpendicular to a chosen MPR direction. By using a corresponding selection user command, the MPR direction may be defined as the direction of the virtual assistance line 23 shown with respect to the real patient 21 on the patient table 4, which is, as noted above, registered to the three-dimensional image data set 27. In this embodiment, it is also provided to use the smart glasses 6, in particular, the projection unit 9 as a display device for displaying the three-dimensional image data set 27 at the position where it was acquired from the patient 21, providing the illusion of a "window" into the patient for the user 20.

Other ways to display image data sets 27 and to define geometrical display parameters are also conceivable.

It is to be understood that the elements and features recited in the appended claims may be combined in different ways to produce new claims that likewise fall within the scope of the present disclosure. Thus, whereas the dependent claims appended below depend from only a single independent or dependent claim, it is to be understood that these dependent claims may, alternatively, be made to depend in the alternative from any preceding or following claim, whether independent or dependent, and that such new combinations are to be understood as forming a part of the present specification.

While the present disclosure has been described above by reference to various embodiments, it may be understood that many changes and modifications may be made to the described embodiments. It is therefore intended that the foregoing description be regarded as illustrative rather than limiting, and that it be understood that all equivalents and/or combinations of embodiments are intended to be included in this description.

The invention claimed is:

1. A method for operating a medical imaging device, the method comprising:
    providing the medical imaging device comprising a user interface device and at least one component, wherein the user interface device comprises a pair of mixed reality smart glasses;
    displaying information relevant to an imaging process in field of view of the smart glasses;
    projecting a virtual assistance line into a field of view of the smart glasses, the virtual assistance line indicating a direction of view of a wearer of the smart glasses;
    receiving a fixing user command;
    holding in place, based on the received fixing user command, a current position of the projected virtual assistance line independently of any movement of the smart glasses;
    receiving an additional user command to control the at least one component of the medical imaging device; and
    controlling the at least one component based on the received additional user command and the direction defined by the virtual assistance line.

2. The method of claim 1, wherein the direction of view of the wearer is defined as being perpendicular to a connecting axis of eyes of the user at a center point between the eyes.

3. The method of claim 1, wherein the virtual assistance line is only shown when a corresponding operating mode has been activated by the user wearing the smart glasses.

4. The method of claim 1, further comprising:
  detecting real objects, virtual objects, or both the real objects and the virtual objects in the field of view; and
  cutting off the projection of the virtual assistance line where the virtual assistance line intersects with at least a part of the real objects and/or the virtual objects.

5. The method of claim 1, further comprising:
  providing at least one selection user command; and
  using a current direction of the virtual assistance line for performing a function associated with the selection user command.

6. The method of claim 5, further comprising, upon detection of a corresponding selection user command:
  selecting at least one geometric acquisition parameter of the medical imaging device dependent on the direction of the virtual assistance line; or
  adjusting at least one interventional component of the medical imaging device dependent on the direction of the virtual assistance line; or
  selecting the at least one geometric acquisition parameter and adjusting the at least one interventional component of the medical imaging device dependent on the direction of the virtual assistance line.

7. The method of claim 6, wherein the medical imaging device is a robot.

8. The method of claim 6, wherein the medical imaging device is a c-arm device, and
  wherein the c-arm device is adjusted such that the acquisition direction corresponds to the direction of the assistance line.

9. The method of claim 5, further comprising, upon detection of a corresponding selection user command:
  choosing at least one geometrical display parameter for displaying an image data set on a display device of the user interface device dependent on the direction of the assistance line.

10. The method of claim 9, wherein the image data set is a three-dimensional image data set of a patient currently imaged with the medical imaging device and registered to a current position of the patient, and
  wherein the direction of the virtual assistance line defines a viewing direction of a presentation of the three-dimensional image data set or a slice stacking direction as the geometric display parameter.

11. The method of claim 10, wherein the three-dimensional image data set or the slice stacking direction is for a multi planar reformation.

12. The method of claim 9, wherein the smart glasses are used as the display device or part of the display device, wherein the image data set is a three-dimensional image data set of a patient currently imaged with the medical imaging device and registered to a current position of the patient and the image data set is projected into the field of view to appear at a position of the patient corresponding to a region of the patient shown in the image data set.

13. The method of claim 1, wherein multiple assistance lines are projected at the same time, corresponding to different users wearing smart glasses and/or including assistance lines held in position due to a corresponding fixing user command.

14. The method of claim 1, further comprising:
  calculating at least one geometry information regarding at least one assistance line; and
  projecting the at least one geometry information into the field of view of the smart glasses.

15. The method of claim 1, further comprising:
  detecting changes in the direction of view of the user, upon activation of a remote control mode; and
  moving a fixed assistance line, which does not indicate the direction of view of the user, according to the detected changes.

16. A medical imaging device comprising:
  a user interface device comprising a pair of mixed reality smart glasses, wherein the user interface is configured to display information relevant to an imaging process to a user, receive user input relevant to an imaging process, or a combination thereof;
  at least one component controllable according to a user command entered using the user interface device; and
  a control device configured to:
    display information relevant to the imaging process in field of view of the smart glasses;
    project a virtual assistance line into a field of view of the smart glasses, the virtual assistance line indicating a direction of view of a wearer of the smart glasses;
    receive a fixing user command;
    hold in place, based on the received fixing user command, a current position of the projected virtual assistance line independently of any movement of the smart glasses;
    receive an additional user command to control the at least one component of the medical imaging device; and
    control the at least one component based on the received additional user command and the direction defined by the virtual assistance line.

17. A method for operating a medical imaging device, the method comprising:
  providing the medical imaging device comprising a user interface device and at least one component, wherein the user interface device comprises a pair of mixed reality smart glasses;
  displaying information relevant to an imaging process in field of view of the smart glasses;
  projecting a virtual assistance line into a field of view of the smart glasses, the virtual assistance line indicating a direction of view of a wearer of the smart glasses;
  receiving a user command to control the at least one component of the medical imaging device; and
  controlling the at least one component based on the received user command and the direction defined by the virtual assistance line,
  wherein the direction of the virtual assistance line defines a slice stacking direction as a geometric display parameter and scrolling user commands are provided, and
  wherein, upon detection of a scrolling user command, an adjacent slice in a scrolling direction associated with or derivable from the scrolling user command is displayed.

18. The method of claim 17, wherein the scrolling user command is a gesture.

* * * * *

UNITED STATES PATENT AND TRADEMARK OFFICE
CERTIFICATE OF CORRECTION

PATENT NO. : 10,682,767 B2
APPLICATION NO. : 16/101673
DATED : June 16, 2020
INVENTOR(S) : Alexander Grafenberg et al.

It is certified that error appears in the above-identified patent and that said Letters Patent is hereby corrected as shown below:

In the Claims

Column 10, (Claim 2; Lines 62-64):
"connecting axis of eyes of the user at a center point between the eyes."

Should be replaced with:
"connecting axis of eyes of the wearer at a center point between the eyes of the wearer."

Column 10, (Claim 3; Line 67):
"has been activated by the user wearing the smart glasses."

Should be replaced with:
"has been activated by the wearer wearing the smart glasses."

Column 11, (Claim 8; Lines 29-31):
"wherein the c-arm device is adjusted such that the acquisition direction corresponds to the direction of the assistance line"

Should be replaced with:
"wherein the c-arm device is adjusted such that an acquisition direction corresponds to the direction of the virtual assistance line"

Column 11, (Claim 9; Lines 37-38):
"user interface device dependent on the direction of the assistance line"

Should be replaced with:
"user interface device dependent on the direction of the virtual assistance line"

Signed and Sealed this
Twentieth Day of October, 2020

Andrei Iancu
*Director of the United States Patent and Trademark Office*

CERTIFICATE OF CORRECTION (continued)
U.S. Pat. No. 10,682,767 B2

Column 11, (Claim 13; Line 58):
"lines are projected at the same time, corresponding to"

Should be replaced with:
"lines are projected at a same time, corresponding to"

Column 12, (Claim 15; Line 7):
"detecting changes in the direction of view of the user,"

Should be replaced with:
"detecting changes in the direction of view of the wearer,"

Column 12, (Claim 15; Line 9):
"direction of view of the user, according to the detected"

Should be replaced with:
"direction of view of the wearer, according to the detected"

Column 12, (Claim 16; Line 13):
"smart glasses, wherein the user interface is configured"

Should be replaced with:
"smart glasses, wherein the user interface device is configured"